(12) United States Patent
Kondo et al.

(10) Patent No.: US 6,613,522 B2
(45) Date of Patent: Sep. 2, 2003

(54) METHOD OF RECONSTITUTING A DNA LIBRARY USING RECA PROTEIN

(75) Inventors: Kazuhiro Kondo, Chiba (JP); Osamu Ohara, Chiba (JP); Michio Oishi, Chiba (JP)

(73) Assignees: Aisin Cosmos R&D Co., Ltd., Aichi-ken (JP); Kazusa DNA Research Institute Foundation, Chiba (JP)

( * ) Notice: Subject to any disclaimer, the term of this patent is extended or adjusted under 35 U.S.C. 154(b) by 143 days.

(21) Appl. No.: 09/872,843

(22) Filed: Jun. 1, 2001

(65) Prior Publication Data

US 2002/0058268 A1 May 16, 2002

(30) Foreign Application Priority Data

Jun. 7, 2000 (JP) ........................................ 2000-170800

(51) Int. Cl.⁷ ............................. C12Q 1/68; C12Q 1/00; C12N 15/00; C12P 21/06
(52) U.S. Cl. ............................ 435/6; 435/4; 435/172.3; 435/320.1; 435/69.1
(58) Field of Search ...................... 435/6, 320.1, 172.3, 435/4, 69.1; 530/350; 514/44

(56) References Cited

U.S. PATENT DOCUMENTS 6,335,164 B1 * 1/2002 Kigawa et al. ................. 435/6

OTHER PUBLICATIONS

M. de Fatima et al., "Normalization and Subtraction: Two Approaches to Facilitate Gene Discovery," Genome Research, Cold Spring Harbor Laboratory Press, 1996, pp. 791–806.
L. Diatchenko et al., "Suppression Subtractive Hybridization: A Versatile Method for Identifying Differentially Expressed Genes," Academic Press, 1999, pp. 349–380.
J. Rubenstein et al., "Subtractive Hybridization System Using Single-Stranded Phagemids with Directional Inserts," Nucleic Acids Research, vol. 18, No. 16, 1990, pp. 4833–4832.

* cited by examiner

*Primary Examiner*—Bennett Celsa
*Assistant Examiner*—Jon D. Epperson
(74) *Attorney, Agent, or Firm*—Christensen O'Connor; Johnson Kindness PLLC

(57) ABSTRACT

The present invention provides a method of constructing a DNA library having increased proportion of a desired nucleic acid(s) therein by removing a nucleic acid(s) other than the desired nucleic acid(s) from a parent library.

8 Claims, 2 Drawing Sheets

METHOD OF RECONSTITUTING A DNA LIBRARY USING RECA PROTEIN

CROSS-REFERENCE TO RELATED APPLICATIONS

This application is based upon and claims the benefit of priority from the prior Japanese Patent Applications No. 2000-170800, filed Jun. 7, 2000, the entire contents of which are incorporated herein by reference.

BACKGROUND OF THE INVENTION

1. Field of the Invention

The present invention relates to a method of constructing a DNA library having increased proportion of a desired nucleic acid(s) therein by removing, from a parent DNA library, a nucleic acid(s) other than the desired nucleic acid(s) using RecA protein.

2. Description of the Related Art

A DNA library, particularly a cDNA library, is a very useful tool for gene cloning. To date, various genes have been cloned from cDNA libraries. A cloned gene is used not only to determine its nucleotide sequence but also to determine amino acid sequence of a protein encoded by the gene and to produce a large amount of the protein in bacterial or yeast cells.

However, cDNAs that can be easily cloned from a cDNA library are restricted to those whose template mRNAs are abundantly expressed in a cell. Hence, cDNAs easy to be cloned have now mostly been cloned, and it is getting harder to clone a novel cDNA with high efficiency.

In order to clone a novel cDNA efficiently from a cDNA library, it is necessary to remove cDNAs already cloned from the library. For this purpose, the following prior arts have been devised.

Subtractive hybridization has been used primarily for this purpose. In the method, mRNAs are harvested both from cells (or tissues) expressing a gene(s) of interest and cells not expressing. Then, from mRNAs of the former cells, cDNAs are synthesized. Through hybridization of the cDNAs with the mRNAs from the latter cells, cDNAs that are present in both cells are selectively removed. This enables enrichment and isolation of a gene(s) specifically expressed in a tissue or a cell.

"Genome Res. 1996 Sep: 6(9): p.791–806" discloses subtractive hybridization using a hydroxyapatite column. In this method, primers from vector-derived sequences are elongated using a single-stranded DNA library as templates. After denaturation and annealing, DNAs that form a double strand again are specifically removed by a hydroxyapatite column. Since probability of annealing is dependent on concentration, abundant clones are preferentially removed.

However, this method can only be applied to a relatively short cDNA of approximately 0.4–2.5 kb. Because non-specific hybridization is likely to occur, when a cDNA library is used which includes a long sequence having an insert size greater than 3 kb. A long sequence is often found to be a functionally important gene encoding a multifunctional protein or a protein with complex conformation. Therefore, it is a major drawback of this method that it cannot be applied to a library containing a long sequence. Furthermore, this method cannot distinguish even short cDNAs, if sequences of the cDNAs are derived from an identical gene and having common sequences at 3' and 5' ends but not in their central regions.

Other method widely used for a similar purpose is differential hybridization.

In this method, cDNA probes are synthesized with mRNAs prepared from control cells and cells of interest from which a specific gene is obtained. A cDNA library generated from the cells of interest is then plated, and colonies on one plate are replica-plated onto two filters. For one filter, hybridization is performed with cDNA probes from the cells of interest. For the other, hybridization is performed with cDNA probes from the control cells. cDNAs specific for the cells of interest can be detected by comparing the results.

However, in this method, differences in hybridization between two filters must be compared from colony to colony. Accordingly, it is difficult to deal with numerous colonies by means of the method. This method is thus not suitable for reconstruction of a whole library. This method has also a drawback of being time-consuming for checking many possible pseudo-positive or pseudo-negative signals.

To overcome such drawbacks of this method, "Methods in Enzymology 1995: 254: p.304–321" discloses differential display method, which is a combination of conventional differential hybridization and polymerase chain reaction (hereinafter referred to as "PCR"). However, this method can detect a difference in a pattern only when a difference in an expression level is significant. Furthermore, since this method cannot produce clones directly, it is necessary to select clones by any method based on a PCR product.

BRIEF SUMMARY OF THE INVENTION

The present invention is made to solve above problems resided in prior arts. Accordingly, the object of the invention is to provide a method that is capable of specifically enriching a desired DNA with a long insert size in a DNA library, and directly providing a clone of the DNA.

To solve the above problems, the invention provides a method of constructing a DNA library having increased proportion of a first double-stranded DNA to be raised in its ratio by removing, from a parent DNA library, a second double-stranded DNA that is not identical to the first double-stranded DNA, the method comprises the following steps of;

(a) converting the first double-stranded DNA and the second double-stranded DNA in the parent DNA library into a corresponding first single-stranded DNA and a second single-stranded DNA respectively, to prepare a library containing the first single-stranded DNA and the second single-stranded DNA;

(b) adding, to the library prepared in the step (a), RecA protein and a linear double-stranded DNA homologous to the second single-stranded DNA to regenerate the second double-stranded DNA from the second single-stranded DNA thereby preparing a library containing the first single-stranded DNA and a regenerated second double-stranded DNA;

(c) removing the regenerated second double-stranded DNA from the library prepared in the step (b);

(d) regenerating the first double-stranded DNA from the first single-stranded DNA thereby constructing a DNA library having increased proportion of the first double-stranded DNA therein.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The present invention provides a method of constructing a DNA library having increased proportion of a desired nucleic acid by removing a specific DNA from a parent DNA library using RecA protein.

As used herein, "RecA protein" means a protein involved in homologous recombination and DNA repair in *E. Coli* and lambda phage as well as in expression of SOS gene in *E. Coli*.

Figure 1:
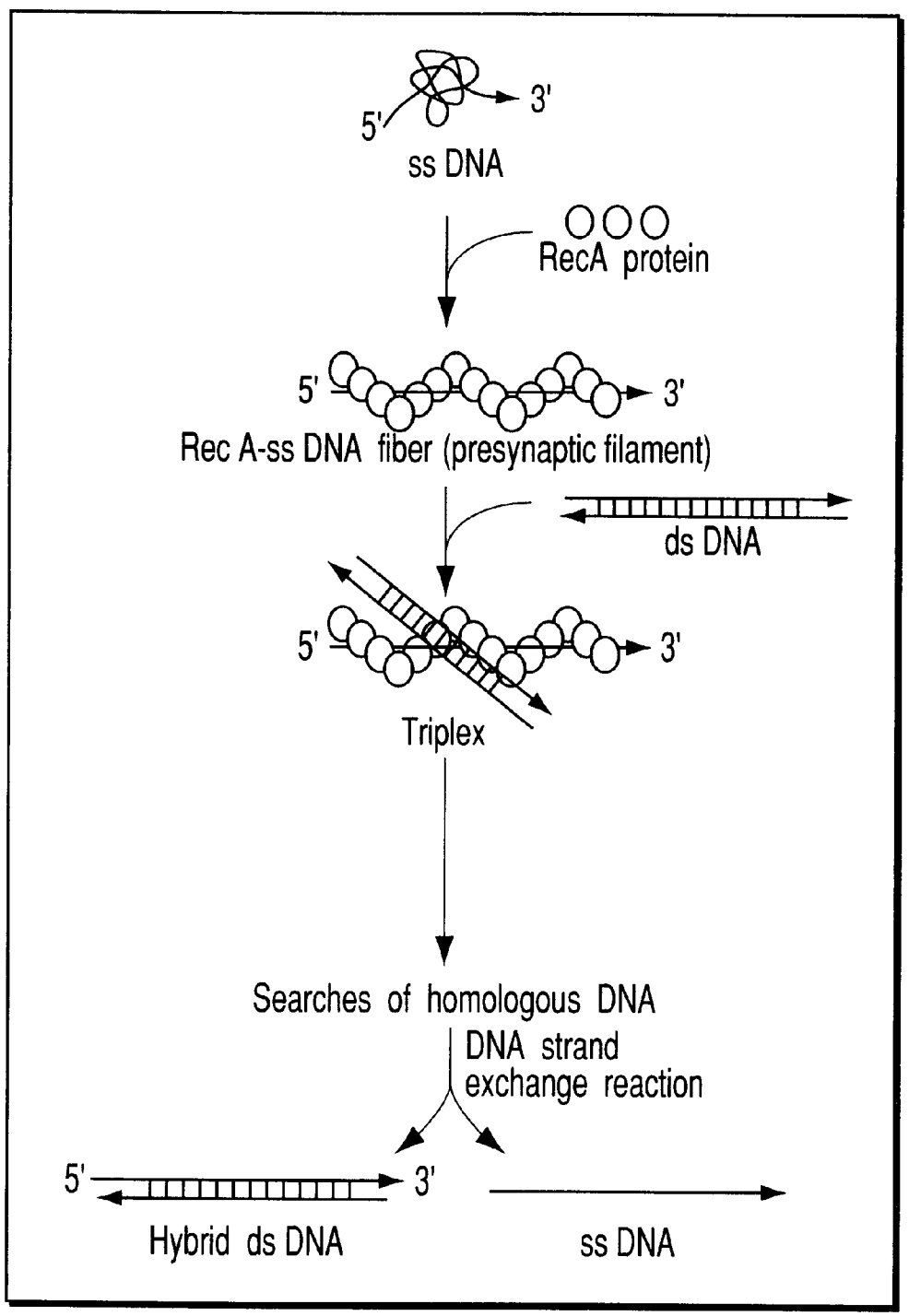
FIG. 1 shows an outline of DNA strand exchange reaction by RecA protein, which is used for the present invention.

As shown in FIG. 1, RecA protein binds to a single-stranded DNA (RecA-ssDNA fiber) and associates the single-stranded DNA with a double-stranded DNA to form a triplex (single-stranded DNA and double-stranded DNA are hereinafter referred to as ssDNA and dsDNA, respectively). The RecA protein then searches for a homologous DNA, and catalyzes DNA strand exchange reaction in the presence of ATP. After the reaction, a hybrid dsDNA, which consists of the dsDNA into which the ssDNA is incorporated, and an ssDNA excised from the dsDNA are formed.

The method of the invention makes use of exchange reaction by RecA protein between ssDNA and dsDNA homologous thereto in order to remove a defined DNA from a DNA library.

It is known that proteins that have similar structure to RecA protein and promote association of homologous DNAs are widely spread in a variety of organisms including prokaryotes other than *E. Coli* and eukaryotes. Such proteins are generally referred to as RecA-like proteins.

As described above, the method of the invention makes use of a function of RecA protein promoting the association of a homologous DNA and catalyzing homologous recombination. Accordingly, the RecA-like proteins could also be used for the method of the invention.

In the term "RecA protein" are therefore included the RecA-like proteins as well as the RecA proteins derived from *E. Coli* and lambda phage.

Preferable RecA protein used for the invention is RecA protein of *E. Coli*.

The term "DNA library" is used herein as a general term referring both to a gene library and a cDNA library. The "gene library" means a panel of phages or cosmids containing fragments of all genomic DNAs in a single species. It is equivalent to a "Genomic DNA library". The "cDNA library" means a panel of various cDNA species produced by inserting, into vectors, complementary DNAs (hereinafter referred to as cDNAS) prepared from mRNAs derived from a given tissue or a cell.

The method of the invention is described in detail hereinbelow.

In the first step of the method, dsDNAs in a parent DNA library, which are a first dsDNA to be raised in its ratio and a second dsDNA to be removed from the library (the second dsDNA is not identical to the first dsDNA), are converted into ssDNAs.

The first and the second dsDNA may be 3–13 kb in size. They are preferably size-fractionated DNAs in a library with a molecular weight of over 6 kb.

Figure 2:
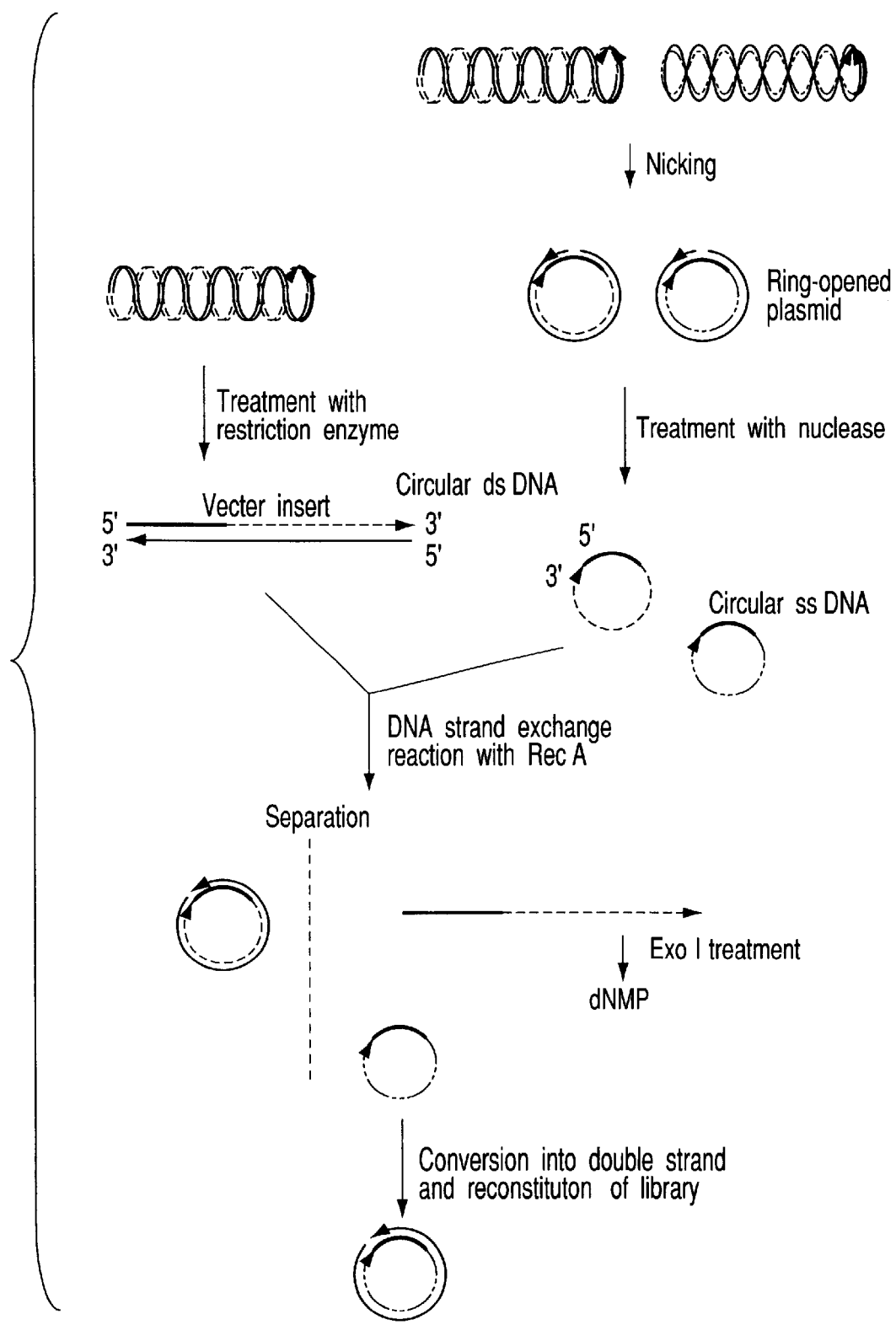
FIG. 2 shows an outline of a method of the present invention.

As shown in FIG. 2, dsDNAs in the library may be converted into ssDNAs by introduction of a nick by e.g. nickase followed by treatment with nuclease such as ExoIII and T7 gene 6.

dsDNAs can also be converted to ssDNAs, but not limited to, by recovering ssDNAs using a phagemid vector such as pBluescript, pGEM, and puc199 as a phage particle.

After this procedure, the first dsDNA and the second dsDNA are converted to the first ssDNA and the second ssDNA respectively to prepare a library containing the first and the second ssDNA.

These dsDNAs included in this library will usually be carried by plasmid or virus vectors.

Subsequently, to the library are added RecA protein and a linear dsDNA homologous to the second ssDNA.

As used herein, a linear dsDNA "homologous" to the second ssDNA to be removed contains, in either strand, a nucleotide sequence substantially identical to the whole or part of the second ssDNA. As used herein, "a nucleotide sequence substantially identical" means that the nucleotide sequence is equivalent enough for allowing the progress of homologous recombination by RecA protein.

Typically, the linear dsDNA may be prepared by giving treatment with a restriction enzyme to a dsDNA completely identical to the second dsDNA. The restriction enzyme preferably cuts only one site in the homologous dsDNA. For example, restriction enzymes can be used which are capable of cutting a restriction site in a vector, when the dsDNAs in the library are carried by vectors.

In either strand in the prepared linear homologous dsDNA, a nucleotide sequence identical to the whole or part of the second ssDNA is contained. Therefore, exchange reaction starts, when the linear dsDNA is mixed with RecA protein and the second ssDNA prepared in a previous step. After the reaction, the second ssDNA is incorporated into the linear homologous dsDNA through exchange with one strand in the dsDNA (See FIG. 2).

The exchange reaction by RecA protein has an orientation. For example, when the linear dsDNA and the circular ssDNA in FIG. 2 are exchanged, the circular ssDNA, which is incorporated into the linear dsDNA, first associates with a 3' side of a strand in the linear dsDNA left unexchanged in the reaction (the upper strand of the circular dsDNA in FIG. 2; hereinafter referred to as an unexchanged strand).

Accordingly, if a sequence complementary to a common sequence of the ssDNAs in the library (e.g. the vector in FIG. 2) is located in the 3' side of the unexchanged strand, all the ssDNAs in the library will be bound to the linear dsDNA, thereby the exchange reaction will be inhibited. Therefore, the common sequence is preferably located in the 5' side of the unexchanged strand in the linear dsDNA.

Since the exchange reaction by RecA protein will be promoted by removal of a linear ssDNA excised from the homologous dsDNA, an excised ssDNA may desirably be degraded during the reaction. To degrade the excised ssDNA, enzymes may preferably be used which do not degrade the rest of ssDNAs. As shown in FIG. 2, only ssDNA excised from the homologous dsDNA can be degraded with exonuclease such as exonuclease I, when the excised ssDNA is linear and the rest are circular.

As described above, specific ssDNA can be removed from a library by means of RecA protein.

After the exchange reaction, the homologous dsDNA (in which DNA to be removed from the library is incorporated) and the ssDNA to be raised in its ratio are separated.

For example a hydroxyapatite column can be used to separate the ssDNA and the dsDNA. Centrifugation in the presence of ethidium bromide as well as combination of restriction endonuclease and magnesium-phenol extraction can also be used, but not limited to, to separate the ssDNA and the dsDNA. See "Nucleic Acids Research, Vol. 18, No. 16, p.4833–4842" for details of these methods.

Finally, conversion of the ssDNA to be raised in its ratio into the corresponding dsDNA results in the library having increase proportion of a desired dsDNA.

Each step described above may be repeated twice or more.

For convenience, one out of two dsDNAs is removed in FIG. 2 and the description above. However, please note, according to the method, dozens to tens of thousands of dsDNAs can simultaneously or sequentially be removed from thousands to tens of thousands of dsDNAs.

As demonstrated in the following Examples, removal of more than 90% of a known dsDNA can be achieved by the method of the invention.

Therefore, a novel clone can be found out from a library with 10–90% increased probability, depending on a type of the library to be used.

The present invention is further illustrated below in more detail referring to the Examples.

EXAMPLE 1

In this example, plasmid A10 was removed from a mixture of two plasmids A10 and B3 by the exchange reaction using RecA protein to increase proportion of B03.

A reaction mixture was added to the two plasmids to carry out the exchange reaction. The mixture contains, in 20 μl, 25 mM Tris-acetate (pH 7.2), 10 mM magnesium acetate, 50 mM potassium glutamate, 1 mM DTT, circular ssDNAs prepared from the plasmids, a linear dsDNA prepared by cleaving one site in the A10 plasmid with NotI, 2.5 mM ATP, 50 mM creatine phosphate, 2 μg of creatine kinase, 0.22 μg of ssDNA binding protein, 1 μg of RecA protein, and 10 units of exonuclease I.

20 μl of the mixture containing 100 ng of the circular ssDNA and 200 ng of the linear dsDNA was reacted at 37° C. for 2 hours under optimal condition.

After deproteinization, circular ssDNAs and dsDNAs were separated.

After deproteinization, circular ssDNAs and a linear dsDNA derived from a vector (digest of pBluescript with SKII(+)/BssHII) were converted to dsDNAs by the exchange reaction using RecA protein. After repair with Vent polymerase, they were introduced into E. Coli and colonies present were counted.

As shown in the Table 1 below, approximately 96% of the A10 plasmid was removed, when the linear dsDNA was added which has an identical sequence with A10 plasmid. In contrast, B03 plasmid was not removed at all, because it has no common sequence with the linear dsDNA except a vector portion.

TABLE 1

| ss-plasmid | number of E. Coli colonies | |
|---|---|---|
| | before removal | after removal |
| A10 alone | 1056 | 41 |
| B03 alone | 1024 | 1140 |

EXAMPLE 2

In this example, known plasmids (3000 clones) were removed from a plasmid library by the exchange reaction using RecA protein.

A reaction mixture was added to the two plasmids to carry out the exchange reaction. The mixture contains, in 20 μl, 50 mM Tris-acetate (pH 7.2), 10 mM magnesium acetate, 50 mM potassium glutamate, 1 mM DTT, 1 μg of circular ssDNAs prepared from the library, 2 μg of a linear dsDNA prepared by cleaving one site in plasmid DNA with NotI, 2.5 mM ATP, 50 mM creatine phosphate, 20 μg of creatine kinase, 2.2 μg of ssDNA binding protein, 10 μg of RecA protein, and 10 units of exonuclease I.

After deproteinization, the reaction was carried out at 37° C. for 2 hours followed by separation of circular ssDNAs and dsDNAs.

After deproteinization, the reaction was repeated to remove known plasmids from a panel of resultant circular ssDNAs.

Finally, after deproteinization, circular ssDNAs and a linear dsDNA derived from a vector (digest of pBluescript with SKII(+)/BssHII) were converted to dsDNAs by the exchange reaction using RecA protein. After repair with Vent polymerase, they were introduced into E. Coli to reconstruct the library.

96 clones randomly selected from each library were sequenced. Frequency of occurrence for unknown clones was evaluated by comparing the determined sequences with a database of known clones.

As shown in Table 2, frequency of occurrence for a novel clone was raised from about 60% up to about 80% by removing known clones once or twice.

TABLE 2

| Library | frequency of occurrence for a novel clone |
|---|---|
| before removal | 58.3% |
| after 1st removal | 74.0% |
| after 2nd removal | 77.1% |

According to the method of the present invention, a DNA library having increased proportion of a desired nucleic acid therein can directly be constructed by removing nucleic acids other than the desired nucleic acid from a parent DNA library.

The method of the present invention may be applied to remove nucleic acids of 3–13 kb in size.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A method of constructing a DNA library having increased proportion of a first double-stranded DNA to be raised in its ratio by removing, from a parent library, a second double-stranded DNA that is not identical to the first double-stranded DNA, said method comprises the following steps of;

(a) converting the first double-stranded DNA and the second double-stranded DNA in the parent library into a corresponding first single-stranded DNA and a second single-stranded DNA respectively, to prepare a library containing the first single-stranded DNA and the second single-stranded DNA;

(b) adding, to the library prepared in the step (a), RecA protein and a linear double-stranded DNA homologous to the second single-stranded DNA to regenerate the second double-stranded DNA from the second single-stranded DNA thereby preparing a library containing the first single-stranded DNA and a regenerated second double-stranded DNA;

(c) removing the regenerated second double-stranded DNA from the library prepared in the step (b);

(d) regenerating the first double-stranded DNA from the first single-stranded DNA thereby constructing a DNA library having increased proportion of the first double-stranded DNA therein.

2. A method according to claim 1, wherein the first and second double-stranded DNA in the library are carried by plasmid vectors.

3. A method according to claim 2, wherein the step (a) comprises introduction of a nick into the double-stranded DNAs with nickase followed by treatment with nuclease.

4. A method according to claim 2, wherein the linear double-stranded DNA in the step (b) is prepared by treating a double-stranded DNA completely identical to the second double-stranded DNA with a restriction enzyme.

5. A method according to claim 4, wherein the linear dsDNA is carried by a vector, and the restriction enzyme cleaves a restriction site of the vector.

6. A method according to claim 2, wherein the step (b) further comprises selective degradation of a linear single-stranded DNA excised from the double-stranded DNA.

7. A method according to claim 6, wherein the degradation is achieved by exonuclase treatment.

8. A method according to claim 1, wherein the step (c) is achieved using a hydroxyapatite column.

* * * * *

UNITED STATES PATENT AND TRADEMARK OFFICE
CERTIFICATE OF CORRECTION

PATENT NO. : 6,613,522 B2
DATED : September 2, 2003
INVENTOR(S) : K. Kondo et al.

It is certified that error appears in the above-identified patent and that said Letters Patent is hereby corrected as shown below:

Title page,
Item [56], References Cited, OTHER PUBLICATIONS, "4833-4832." should read -- 4833-4842. --.

Column 7,
Line 10, "comprises" should read -- comprising --.
Line 11, "steps of;" should read -- steps of: --.
Line 23, "stranded DNA thereby" should read -- stranded DNA, thereby --.
Line 26, "step (b);" should read -- step (b); and --.

Column 8,
Line 2, "DNA thereby" should read -- DNA, thereby --.

Signed and Sealed this

Twenty-seventh Day of September, 2005

JON W. DUDAS
*Director of the United States Patent and Trademark Office*